United States Patent [19]
Patterson

[11] Patent Number: 6,099,485
[45] Date of Patent: Aug. 8, 2000

[54] TORQUABLE, LOW MASS MEDICAL GUIDEWIRE

[75] Inventor: Frank Van Patterson, Exeter, N.H.

[73] Assignee: C. R. Bard, Inc., Murray Hill, N.J.

[21] Appl. No.: 09/230,383

[22] PCT Filed: Jun. 3, 1997

[86] PCT No.: PCT/US97/11617

§ 371 Date: Jan. 22, 1999

§ 102(e) Date: Jan. 22, 1999

[87] PCT Pub. No.: WO98/08432

PCT Pub. Date: Mar. 5, 1998

Related U.S. Application Data

[60] Provisional application No. 60/024,443, Aug. 27, 1996.

[51] Int. Cl.[7] .......................................................... A61B 5/00
[52] U.S. Cl. ............................................................... 600/585
[58] Field of Search ..................................... 600/434, 585; 604/95, 280–283

[56] References Cited

U.S. PATENT DOCUMENTS

| | | |
|---|---|---|
| 3,789,841 | 2/1974 | Antoshkin . |
| 4,846,193 | 7/1989 | Tremulis et al. . |
| 4,925,445 | 5/1990 | Sakamoto et al. . |
| 5,111,829 | 5/1992 | de Toledo . |
| 5,176,661 | 1/1993 | Evard et al. . |
| 5,241,970 | 9/1993 | Johlin, Jr. et al. . |
| 5,267,573 | 12/1993 | Evans et al. . |
| 5,341,817 | 8/1994 | Viera . |
| 5,363,847 | 11/1994 | Viera . |
| 5,379,779 | 1/1995 | Rowland et al. . |
| 5,409,015 | 4/1995 | Palermo . |
| 5,497,783 | 3/1996 | Urick et al. . |

*Primary Examiner*—Max Hindenburg
*Attorney, Agent, or Firm*—Darby & Darby

[57] ABSTRACT

A guidewire for use in endoscopic retrograde cholangio pancreatography (ERCP) includes a proximal section defined by a fiber rod, a tube, and a connection mechanism for attaching the tube and fiber rod together in a collinear relationship. The guidewire also includes a flexible distal section which is attached to the distal end of the tube. The distal section is comprised of a superelastic core having a radiopaque marker disposed about its distal end, and at least a portion of the distal section is enveloped by an insulative sleeve. The superelastic core may be tapered, and the fiber rod may comprise a multiplicity of fibers encapsulated in a resin.

13 Claims, 4 Drawing Sheets

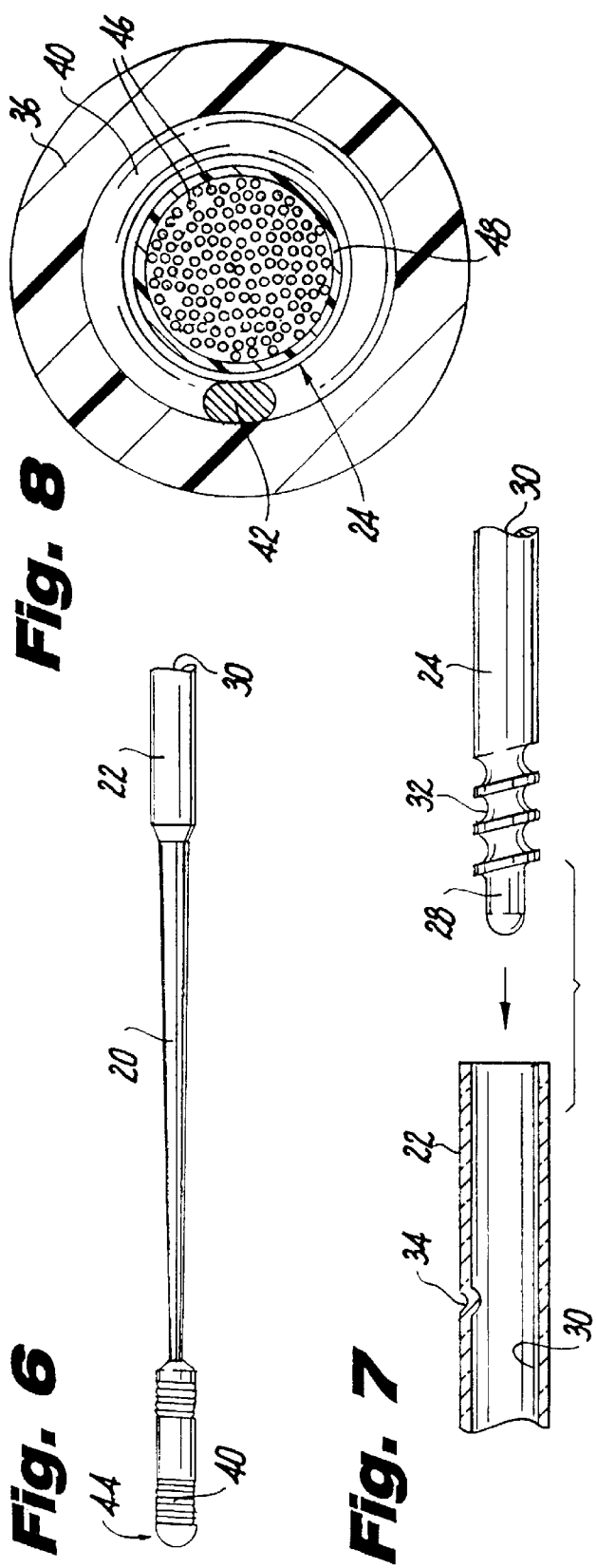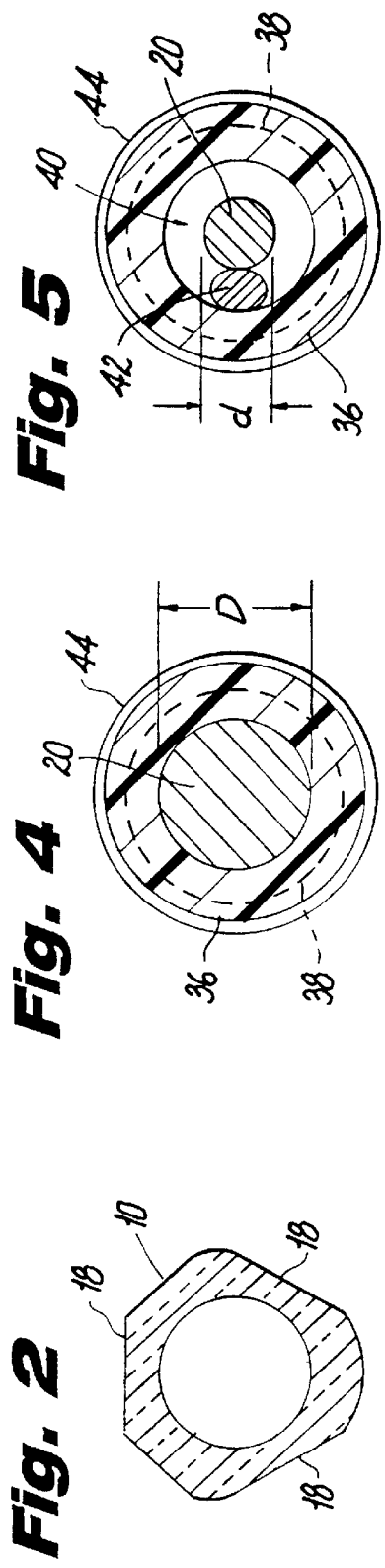

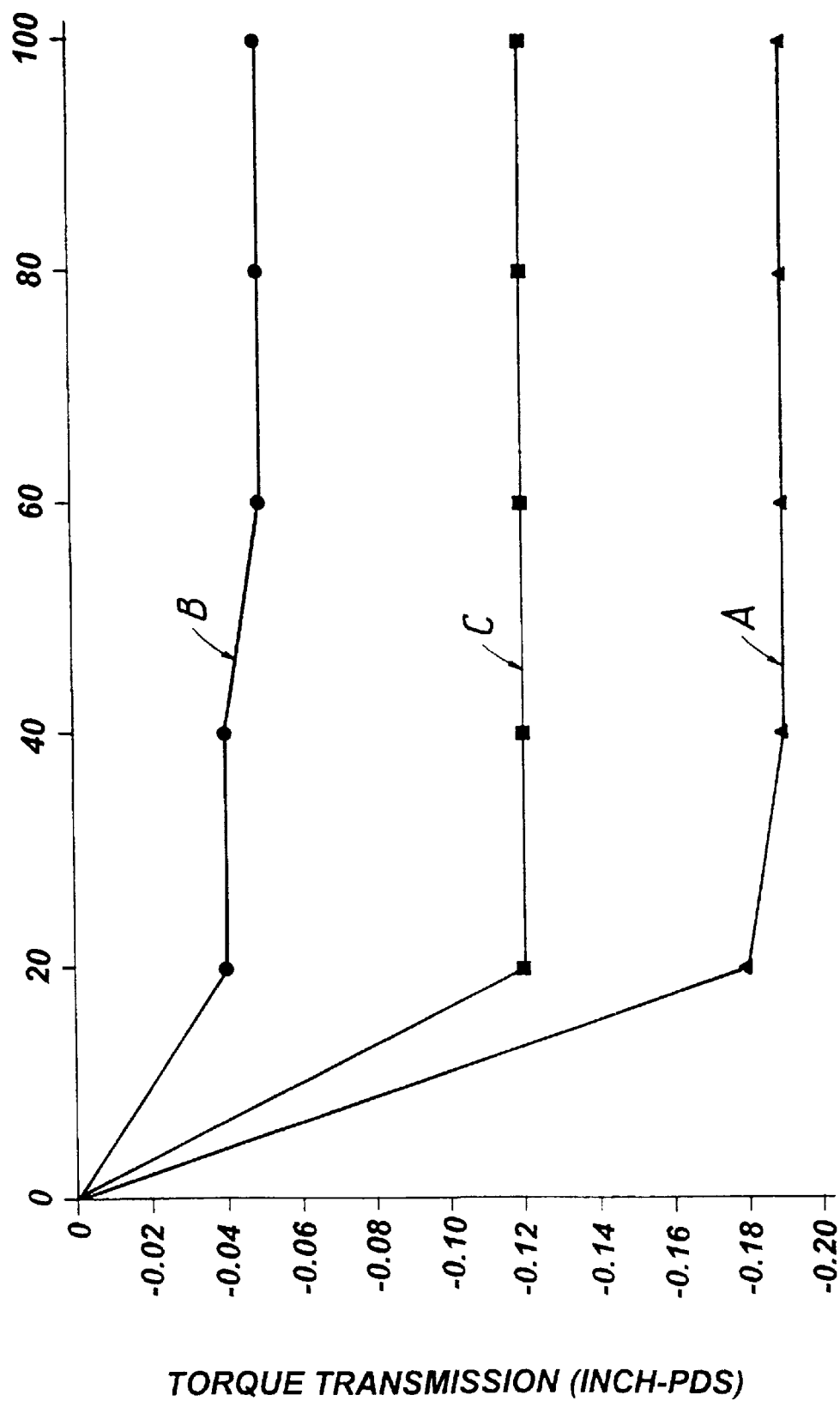

TORQUABLE, LOW MASS MEDICAL GUIDEWIRE

The present application is based upon one Provisional Patent Application Ser. No. 60/024,443 filed Aug. 27, 1996. Applicant claims the benefit of the filing date of the aforesaid provisional application under 35 U.S.C. §119.

FIELD OF THE INVENTION

This invention relates to medical guidewires, and, more particularly, to a torquable, low mass medical guidewire of the type used in endoscopic retrograde cholangeo pancreatography (ERCP).

BACKGROUND OF THE INVENTION

In ERCP, an exchange guidewire is threaded through a lumen or open channel of an endoscope and maneuvered to a designated site within a patient's passageway to serve as a guide for positioning a device which is used to perform a procedure. The procedure may occur within the common bile duct, the cystic duct, the pancreatic duct, or the left or right hepatic duct. The guidewire, the medical instrument, and the area near the papilla of vater or the pancreatic duct are illuminated by a fiber optic light source within the endoscope and may be viewed through the endoscope or on a video monitor using a remote imaging system. The remote imaging system assists the operator and his or her staff to continuously maneuver the guidewire to maintain its position in the ductal anatomy in view of any unexpected endoscope position changes, to compensate for active motility in the gastrointestinal tract, and to maintain guidewire position during catheter exchange procedures.

Typically, the endoscope is introduced orally and maneuvered through the alimentary canal into the duodenum. The guidewire is threaded through a lumen of the endoscope and manipulated by torquing, steering, pushing and pulling to cannulate the papilla and enter the common bile duct and, if necessary, any duct branching therefrom. To withstand these manipulations and facilitate advancement of the guidewire without kinking, the guidewire is typically made of a material that has a handling characteristic which permits the operator to have a sense of the guidewire position without excessive recourse to fluoroscopy, and a strength characteristic that can support the advancement of a medical instrument thereover without the guidewire retracting from a previously accessed duct.

Conventionally, guidewires have been made using stainless steel cores, superelastic alloys such as Nitinol, or combinations of the two. Nitinol is a presently preferred material because of its flexibility; however, Nitinol and other superelastic alloys are expensive and difficult to produce. Further, superelastic alloys do not bond well to other materials, and, as a result, several ERCP guidewires have been constructed entirely of Nitinol, for example, the guidewires described in U.S. Pat. No. 5,379,779 of Rowland et al. and in the product literature for Microvasive's Geenan guidewire. These guidewire constructions are not only expensive to construct, but they provide limited torque (in inch-pounds).

As for guidewire constructions which are only part superelastic, the bond between the superelastic material and the remainder of the guidewire is believed to compromise the guidewire's ability to faithfully transmit torque (that is, cause 360° rotation of the guidewire distal end with equal rotation of the proximal end) across the bond to the guidewire distal end. Further, it has been difficult to produce a highly torquable guidewire of simple construction using superelastic alloys in conjunction with other materials.

One design which has been constructed using a superelastic distal segment in combination with a solid core is disclosed in U.S. Pat. No. 5,111,829 of de Toledo. However, the stainless steel solid core is difficult to join with the Nitinol distal segment, and no attempt is made to reduce the mass of the overall guidewire. Operators of such constructions have had difficulty in directing known guidewires presumably due to inertial forces of the guidewire which result from the transmission of torque to the guidewire distal end. The inertial force tends to cause the guidewire to turn farther than desired (a phenomena known as "whipping") which exacerbates the problem of negotiating tortuous passageways.

OBJECTS AND SUMMARY OF THE INVENTION

It is an object of the invention to provide an improved guidewire for use in endoscopic procedures, particularly ERCP.

It is another object of the invention to provide an exchange length guidewire for use in endoscopic procedures.

It is a further object to provide a highly torquable guidewire that has low susceptibility to whipping.

According to one aspect of the invention, a guidewire for use in endoscopic retrograde cholangio pancreatography includes a proximal section defined by a fiber rod, a tube, and a connection mechanism for attaching the tube and fiber rod together in a collinear relationship. The guidewire also includes a flexible distal section which is attached to the distal end of the tube. The distal section is comprised of a superelastic core having a radiopaque marker disposed about its distal end, and at least a portion of the distal section is enveloped by an insulative sleeve. The superelastic core may be tapered, and the fiber rod may comprise a multiplicity of fibers encapsulated in a resin.

These and other features and advantages of the invention will be readily apparent from the following detailed description of a preferred embodiment taken in conjunction with the accompanying unscaled drawings.

BRIEF DESCRIPTION OF THE DRAWINGS

FIG. 2 is a cross-sectional view of a proximal end of a guidewire according to the a preferred embodiment taken along line 2—2 of FIG. 1;

FIG. 4 is cross-sectional view of the guidewire taken along line 4—4 of FIG. 3;

FIG. 5 is cross-sectional view of the guidewire taken along line 5—5 of FIG. 3;

FIG. 6 is an elevational view of a subassembly of the guidewire;

FIG. 7 is a detailed view, in cross-section, of the guidewire according to a modified embodiment of the invention;

FIG. 8 is a cross-sectional view of the guidewire taken along line 8—8 of FIG. 3;

FIG. 10 is a graphical illustration of normalized torque transmission verses percent of counterclockwise rotation of a guidewire according to the invention.

DETAILED DESCRIPTION OF THE PREFERRED EMBODIMENTS

Figure 1:
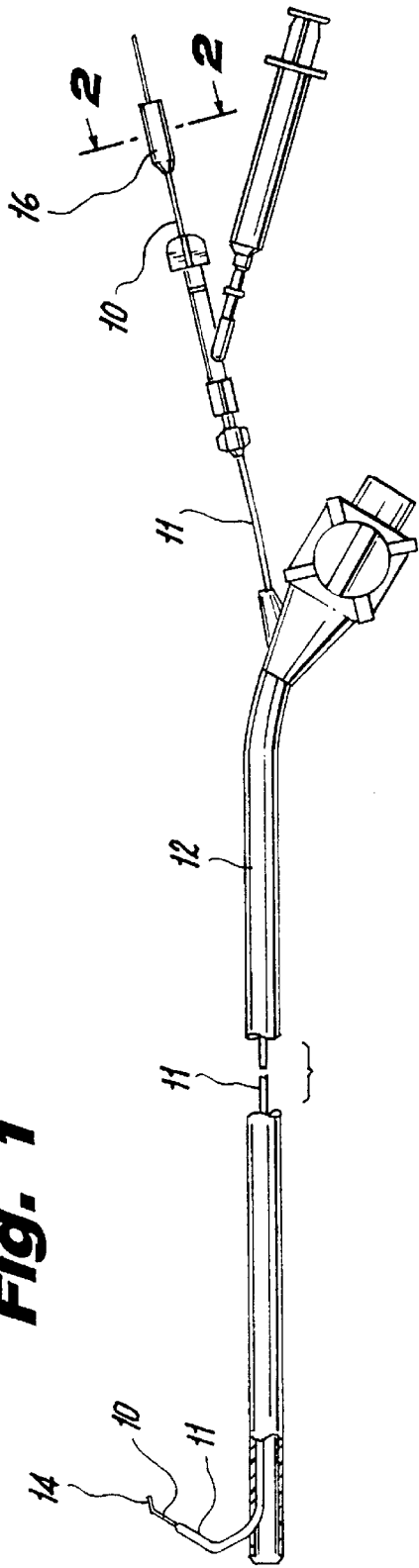
FIG. 1 is a diagrammatic, elevational view of a guidewire threaded into an endoscope.
Figure 3:
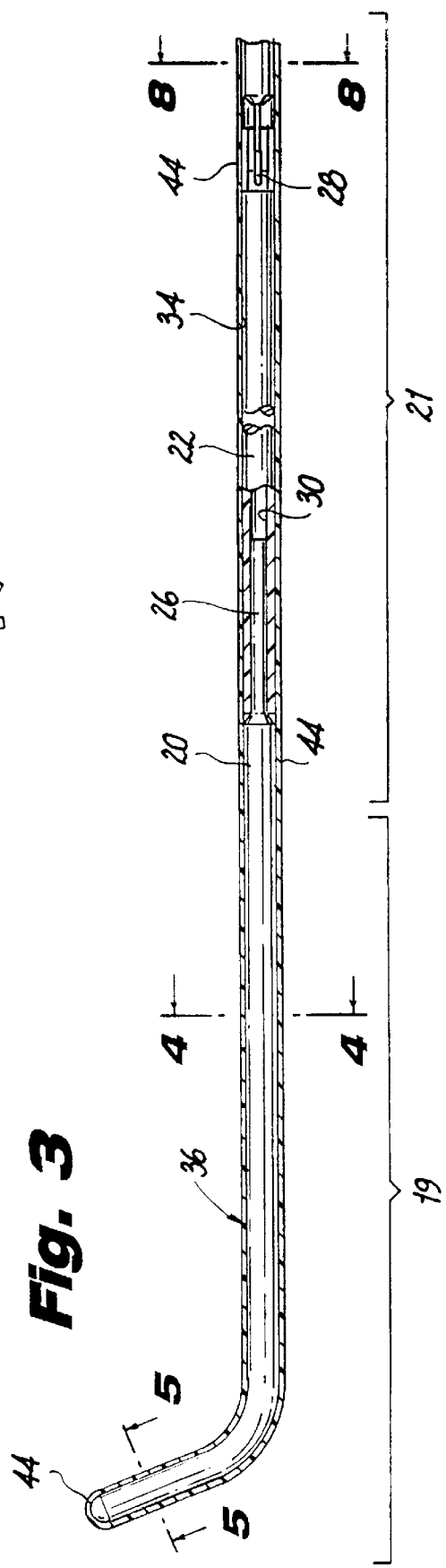
FIG. 3 is an elevational view, partially in cross-section, of a guidewire according to the invention.

By way of overview and introduction, FIG. 1 illustrates an ERCP guidewire 10 having a diameter of about 18 to 35 mils inserted into an endoscope 12. Preferably, the guidewire 10 is about 450 cm long and has a bent distal end 14. The distal end 14 may be formed as a hockey-stick tip (as shown), a J-tip, or other shape as may be desired for a given procedure. The guidewire 10 is advanced beyond the endoscope 12 and steered into the patient's body passageway to a preselected duct.

Because the guidewire 10 is small compared to the operator's fingers, a vice or handle 16 is selectively attached to the guidewire 10 at a point proximal to the proximal end of the endoscope 12 (FIG. 1). Rotation of the comparatively wider vice 16 causes a corresponding rotation of the guidewire distal end 14 within a plane and provides the operator with a sense of the degree of guidewire rotation. In other words, the vice 16 facilitates torquing of the guidewire. By torquing the guidewire 10, the distal tip 14 is directed toward the opening in a side or branching pathway to facilitate advancement of the guidewire 10. The cross-sectional view of FIG. 2 illustrates a plurality of (optional) flattened segments 18 which provide surfaces that are engaged by clamping action of the vice 16 to selectively yet rigidly couple the vice 16 and guidewire 10 together. The vice 16 is removed prior to advancement or withdrawal of a catheter 11 over that portion of the guidewire, and need only be used, if at all, while steering the guidewire 10 to a designated site.

Turning now to FIGS. 3–6, the guidewire 10 according to a preferred embodiment is described. The guidewire 10 generally comprises a distal segment 19 and a proximal segment 21. The distal segment 19 includes a superelastic alloy core 20 (25 cm to 40 cm long), preferably Nitinol, and the proximal segment 21 includes a tubular section 22 (3 cm to 240 cm long) preferably made of stainless steel, a fiber section 24 (180 cm to 220 cm long) preferably made of a glass/epoxy composite and comprising a multiplicity of glass fibers, and an attachment (selective or permanent) which connects the tubular section 22 and the fiber section 24 in a collinear relationship. The alloy core 20 and the fiber section 24 each have a reduced diameter end, 26, 28, respectively, which is shaped to be seated within a lumen 30 of the tubular section 22. The three elongate elements (the alloy core 20, tubular section 22, and fiber section 24) are preferably permanently attached to one another by an adhesive bond, crimping, swaging, or other conventional means. This arrangement provides a particularly strong union between the alloy core 20 and the tubular section 22 for faithful transmission of torque. This is especially important when the alloy core 20 is made of a superelastic alloy because such alloys are well known to be difficult to join to other materials.

In the modified embodiment of FIG. 7, the fiber section 24 is detachable from the tubular section 22 and forms an extension section when connected. The reduced diameter end 28 of the fiber section 24 in this modified embodiment has spiral threading 32 extending therefrom which may be advanced past a dimple 34 in the tubular section 22 by rotation of the fiber section 24 relative to the tubular section 22, whereby the former is engaged to the latter. The threaded distal end 28 is shaped so as to have a maximum outside diameter which closely approximates the inside diameter of the lumen 30 of the tubular section 22. Further details of this construction are provided in U.S. Pat. No. 5,267,573 of Evans and assigned to the present assignee, the disclosure of which is hereby incorporated by reference as if set forth fully herein.

Preferably, the guidewire 10 is jacketed in an electrically insulative cover or coating which may provide a substantially uniform outside diameter to the guidewire 10 from the distal end 14, across the unions of the guidewire segments 19 and 21 and toward the guidewire's proximal end. The distal segment 19 may be covered with a sleeve 36, preferably polyurethane, chosen to be of an elasticity which matches or approximates the elasticity of the alloy core 20.

The sleeve 36 may be a polyimide thermoset resin having steel-braiding 38 impregnated therein to improve the transmission of torque to the distal tip 14 (FIG. 4). Also, the sleeve having the steel-braiding 38 may progressively decrease in stiffness from its proximal to its distal end, for example, by reducing from about 140 PICS/inch at its proximal end near the union with the tubular section 22 to about 60 PICS/inch at the distal tip 14 to enhance the handling characteristics of the guidewire 10, especially if the alloy core 20 tapers toward the distal tip 14. A greatly preferred performance characteristic is that the sleeve 36 be formed from a material which does not deform over the smallest bend radius likely to be encountered during a particular procedure. The sleeve 36 may further have a radiopaque material impregnated therein to facilitate fluoroscopic monitoring.

Turning now to FIG. 5, the alloy core 20 is shown as having tapered from a first diameter D at a proximal portion (FIG. 4) to a second, smaller diameter d at a distal portion. By tapering the alloy core 20, distal flexibility of the guidewire 10 is enhanced and the guidewire distal tip 14 is therefore softer to better ensure an atraumatic insertion into a patient. However, there need not be any taper in the alloy core 20, especially where it is made of a superelastic material; the proximal end of the alloy core 20 may have a diameter which is no greater than the diameter of the distal end of the alloy core 20.

Also illustrated in FIG. 5 is a coil spring 40 disposed about the distal 1 to 10.5 cm of the distal segment 19 (cut through a cross-section 42), and may be secured to the alloy core 20 by a liquid adhesive such as epoxy. The coil spring 40 may be made of a radiopaque material to assist in fluoroscopic monitoring of the guidewire, or may be made of stainless steel wire and have a segment coated with a radiopaque material selected, for example, from the group including platinum, tantalum, tungsten, gold, tantalum oxide, and combinations thereof alone or with other elements. This latter arrangement provides a radiopaque marker without affecting the stiffness properties of the alloy core 20, and hence the handling characteristics of the distal end 14 of the guidewire 10. The coil spring 40 may also be adapted (e.g., by suitable choice of materials or by metal working) to take a set such as the hockey-stick tip shown in FIGS. 1 and 3. (Alternatively, a forming wire may be secured to the alloy core 20, coil spring 40, or sleeve 36 in conventional manner, for example, by soldering, welding, or crimping the forming wire to the distal end of the coil spring 30, melting it to the sleeve 36, adhesively bonding it to the core 20, or any combination of the above.)

Alternatively, spring coils made of different materials may be joined together to space one or more radiolucent coil segments by one or more radiopaque coil segments of a predetermined length, interleaved as disclosed in U.S. Pat. No. 4,922,924 of Gambale et al. and assigned to the present assignee, the disclosure of which is hereby incorporated by reference as if set forth in its entirety herein, stretched to have varying pitch whereby the opacity of a radiopaque coil is modified, provided with a radiopaque polymer filler as a marker (which filler may be thermoset within the coils of a stainless steel coil), and the like.

FIG. 6 shows the spring 40 disposed about the distal end of the alloy core 20 prior to the sleeve 36 being extruded or joined to the alloy core 20/spring coil 40 subassembly. The alloy core 20 is shown having a decreasing diameter from its proximal end to the distal end 14, for example, as a result of taper-grounding a rod of Nitinol material. Although the coil spring 40 is shown having a generally uniform diameter, it could be wound to match a taper in the alloy core 20, if there is any taper. The sleeve 36 is preferably melted to a rounded tip 44 (FIG. 3) and envelopes the alloy core 20 and coil spring 40 to provide a unitary distal segment 19 assembly for insertion into a patient.

Preferably, the tubular section 22 is made of a hyperdermic tube ("hypotube"), for example, #304 stainless steel hypotube or a tubular material of similar rigidity. The applicant has discovered that the low mass of a tube as compared to a solid core reduces the inertial forces transferred to the guidewire distal tip 14. This reduces the tendency of the guidewire 10 to whip while being advanced and steered to a designated site. Thus, the rotational response characteristic (torque transmission) from the proximal end to the distal end of the guidewire is enhanced as compared to conventional ERCP guidewires by constructing the majority of the guidewire 10 from the tubular section 22, i.e., the hypotube.

Figure 9:
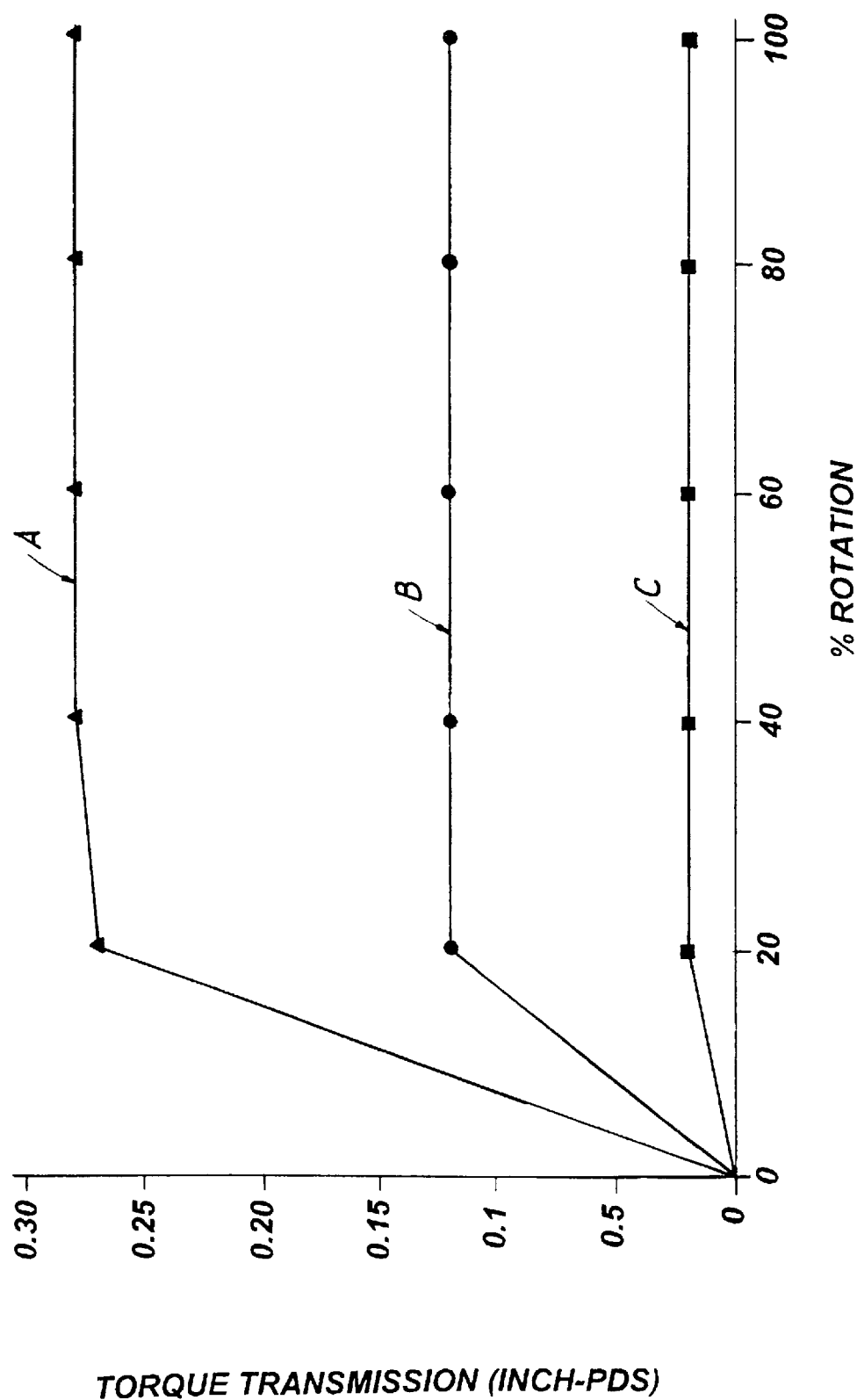
FIG. 9 is a graphical illustration of normalized torque transmission verses percent of clockwise rotation of a guidewire according to the invention.

With reference now to FIGS. 9 and 10, torque transmission verses percent of clockwise (FIG. 9) and counterclockwise (FIG. 10) rotation of the guidewire 10 is illustrated in comparison with two prior art guidewire constructions. The ordinate axis illustrates the normalized energy transmission from the proximal end of a guidewire 10 to the distal tip 14. Perfect transmission has a value of unity, that is no storage of applied energy in the guidewire itself. The abscissa shows rotation of the proximal end of the guidewire as a percentage of 360° (thus, 20% rotation is 720). Curve A is of a guidewire 10 according to the invention in which the fiber section 24 is fixedly attached to the tubular section 22. Curve B is of the Rowland et al. guidewire. Curve C is of the Geenan guidewire. FIGS. 9 and 10 illustrate that the inventive guidewire 10, provides enhanced torque transmission as compared to known ERCP guidewires. The improvement over known designs is directly attributable to the use of tubular section 22 instead of a solid core of Nitinol.

In addition, it has been empirically observed that a generally rigid tubular element can elastically contain stress (by deforming to an oval cross-section) as the guidewire 10 is advanced through bends in a passageway, and is therefore more flexible than a solid core stainless steel construction, yet transmits more torque than a highly flexible guidewire formed entirely from a superelastic alloy as demonstrated in FIGS. 9 and 10. Further, hypotubes are less prone to kinks than solid core constructions of similar outer diameter, and provide a simple attachment to a more proximal segment such as the fiber section 24.

The tubular section 22 is coated or sprayed with a layer of polyimide, polytetrafluoroethylene (Teflon), fluorinated ethylene propylene (FEP), or other material, to provide electrical insulation to this portion of the guidewire 10 and reduce the friction of the outer surface of the guidewire. This layer may be about 0.25 mil to about 1.0 mil thick except perhaps along its most proximal 12 cm where the coating may be thinner or absent for attachment of the vice 16.

The distal segment 19 and the tubular section 22 may be further jacketed in a hydrophilic coating 44 (FIG. 1) such as polyurethane, polyethylene, polyimide, fluoropolymer, or a combination of these materials. A further description of hydrophilic and hydrogel coatings can be found in U.S. Pat. Nos. 5,077,352; 5,179,174; 5,160,790; 5,290,585, all of Richard Elton and assigned to the present assignee, the disclosures of which are hereby incorporated by reference as if set forth in their entirety herein. This hydrophilic coating is secured directly to the outermost surface of the guidewire 10 (including the Nitinol rod 20, sleeve 36, hypotube 22 and perhaps the fiber core 24) to provide a low coefficient of friction.

As illustrated in the cross-section of FIG. 8, the fiber section 24 is preferably a glass/epoxy composite comprising a multiplicity of glass fibers 46 10–15 microns in diameter, preferably 12–14 microns in diameter. Known fibers 46 that can be used in place of glass include aramid (Kevlar), oriented polyolefin (Spectra), and any elongate element which has an overall flex modulus of at least four million pounds per square inch ("psi"), preferably at least seven million psi. The foregoing are illustrative (and not restrictive) of the types of elongate elements that can be used as fibers 46 to form the fiber section 24.

The fibers 46 are encapsulated in an epoxy or polyester thermoset resin 48. The resin 48 encapsulation layer is preferably about 25.4 to about 50.8 microns (about one to about two mils). The resin 48 contributes to the hoop strength of the guidewire 10 and increases the minimum bend radius that the fiber section 24 can withstand without breakage. One suitable glass/epoxy composite is manufactured by Neptco, Inc. of Pawtucket, R.I., and is sold under the trademark LIGHTLINE. The LIGHTLINE glass/epoxy composite includes 1600 fibers in cross-section. The fiber section 24 including fibers 46 and resin 48 preferably has a nominal diameter of about 400 to about 700 microns (about 20 to about 30 mils).

In the illustrated embodiment, a sheath 50 envelopes the fiber section 24 and is bonded thereto. The sheath 50 is preferably plastic, and may be made from fluorinated ethene propene (FEP), polytetrafluoroethylene (TFE), pefluoroalkoxy resin (PFA), chlorinated triflouroethylene (CTFE), polyolefin, polyurethane, polyether amide block copolymer, or the like. The sheath 50 permits the guidewire 10 to bend to a smaller radius with a reduced likelihood of guidewire breakage during storage because it permits the guidewire 10 to be dispensed from a coiled hoop of small radius. The sheath surrounds at least the entire fiber section 24 to provide a generally smooth outer surface to that section of the guidewire 10.

In operation, the guidewire 10 is initially advanced through a lumen of an ERCP cannula, papillotome or other catheter used in the ERCP procedure. The vice 16 is selectively secured at an appropriate point along the proximal end of the tubular section 22 to assist in steering (torquing) the guidewire 10 until the guidewire exits the distal end of the ERCP catheter 11. Once the guidewire 10 has been positioned, as confirmed by fluoroscopic imaging of the area, a catheter 11 can be advanced to the major or minor papilla of Vater, pancreatic or common bile duct, cystic duct, right or left hepatic duct, etc. to perform the required procedure. If a catheter exchange becomes necessary, it can be performed without axially displacing the guidewire 10 by withdrawing the catheter over the fiber section 24, which is either permanently attached to the proximal end of the tubular section 22 or selectively attached for permitting the catheter exchange procedure.

As will be readily apparent to those skilled in the art the dimensions stated relate to one particular guidewire size and are disclosed solely by way of example and should not, therefore, be understood as an intended limitation on the scope of the invention.

It is preferred that the Nitinol have the temperature at which its transformation to austenite is complete be between about 15° C. and 21° C. to ensure that the material is superelastic at the temperatures at which the guidewire 10 is expected to be used.

Having thus described a preferred embodiment of the present invention, it is to be understood that the above described device is merely illustrative of the principles of the present invention, and that other devices may be devised by those skilled in the art without departing from the spirit and scope of the invention as claimed below.

I claim:

1. A guidewire for use in endoscopic retrograde cholangio pancreatography (ERCP), comprising:
    a proximal section comprising a fiber rod, a tube, and means for attaching the tube and fiber rod together in a collinear relationship,
    a flexible distal section, said distal section being attached to the distal end of the tube and comprising
        (i) a superelastic core having a proximal end of a first diameter and a distal end of a diameter no greater than that of said superelastic core wire proximal end, and
        (ii) a radiopaque marker disposed about the distal end of said superelastic core; and
    an insulative sleeve enveloping at least a portion of said distal section.

2. The ERCP guidewire as in claim 1, wherein said superelastic core is tapered.

3. The ERCP guidewire as in claim 2, wherein said radiopaque marker is a coil which is tapered to match the taper of said superelastic core.

4. The ERCP guidewire as in claim 1, wherein the stiffness of said sleeve progressively decreases toward the distal end of the guidewire.

5. The ERCP guidewire as in claim 1, in which said fiber rod comprises a multiplicity of fibers selected from the group consisting of glass, aramid and polyolefin, encapsulated in a material selected from the group consisting of epoxy and polyester thermoset resin.

6. The ERCP guidewire as in claim 5 wherein a plastic sleeve is bonded to the fiber core.

7. The ERCP guidewire as in claim 1, wherein the tube has a non-circular portion which defines an engagement surface to facilitate the application of torque to the guidewire.

8. A guidewire for use in endoscopic retrograde cholangio pancreatography (ERCP), comprising
    a proximal section comprising a fiberglass rod, a hypotube, and means for attaching the hypotube and fiberglass rod together in a collinear relationship,
    a flexible distal section, said distal section being attached to the distal end of the hypotube and comprising
        (i) a Nitinol core having its distal end tapered, and
        (ii) a radiopaque coil secured to the tapered distal end of said Nitinol core; and
    an insulative sleeve enveloping at least a portion of said distal section.

9. The ERCP guidewire as in claim 8 wherein said coil is tapered to match the taper of said Nitinol core.

10. The ERCP guidewire as in claim 8, wherein the stiffness of said sleeve progressively decreases toward the distal end of the guidewire.

11. The ERCP guidewire as in claim 8, in which said fiberglass rod comprises a multiplicity of fibers selected from the group consisting of glass, aramid and polyolefin, encapsulated in a material selected from the group consisting of epoxy and polyester thermoset resin.

12. The ERCP guidewire as in claim 11, wherein a plastic sleeve is bonded to the fiberglass core.

13. The ERCP guidewire as in claim 8, wherein the tube has a non-circular portion which defines an engagement surface to facilitate the application of torque to the guidewire.

* * * * *